United States Patent [19]
Arnold et al.

[11] Patent Number: 5,127,727
[45] Date of Patent: Jul. 7, 1992

[54] ILLUMINATION DEVICES FOR INSPECTION SYSTEMS

[75] Inventors: Aaron L. Arnold, Palm Beach Gardens; Daniel A. Woodward, West Palm Beach, both of Fla.

[73] Assignee: Northern Telecom Limited, Montreal, Canada

[21] Appl. No.: 707,830

[22] Filed: May 30, 1991
(Under 37 CFR 1.47)

[51] Int. Cl.⁵ .................................. G01N 21/88
[52] U.S. Cl. .................................... 356/237
[58] Field of Search .............. 356/237; 358/106; 250/223 B

[56] References Cited

U.S. PATENT DOCUMENTS 4,688,939 8/1987 Ray .......................... 356/237
4,695,157 9/1987 Schoenbaum ............. 356/237

FOREIGN PATENT DOCUMENTS 201241 10/1985 Japan ......................... 356/237
187142 8/1988 Japan ......................... 356/237

Primary Examiner—Richard A. Rosenberger
Attorney, Agent, or Firm—Foley & Lardner

[57] ABSTRACT

An illumination device of an inspection system of circuit board pin extending from a printed circuit board provided with a shroud to prevent reflected light from distorting or otherwise deleteriously affecting the image received by a video camera. In the device, the shroud surrounds the pin and around a passage for directing the camera. The light source is annular and surrounds the shroud with the shroud extending axially from the light source and in the direction of light emitted from the source.

5 Claims, 4 Drawing Sheets

ILLUMINATION DEVICES FOR INSPECTION SYSTEMS

This invention relates to illumination devices for inspection systems.

Illumination devices for inspection systems are of many types, each designed specifically for illuminating certain types and sizes of articles. One particular type of illuminating device for an inspection system is designed to enable printed circuit board pins inserted into a circuit board to be inspected individually so as to determine the spatial position of the free end of the pin and to compare it with a predetermined desirable pin position. For this purpose, the illuminating device provides a source of light which is reflected from a surface of the printed circuit board to a video camera which transmits signals relating to light intensity to a computer wherein the actual comparison analysis takes place. For this operation, the accuracy of pin determination is dependent upon there being a sharpness in edge definition of the free end of the pin and, for this purpose, it is required that the free end of the pin should reflect no light so that its position is abundantly clear when surround by the upwardly reflected light from the printed circuit board. Clarity of definition is indeed important when any horizontal spatial deviation of the free end of the pin by say 0.005 inches from its desired datum position should be determinable by the inspection system. In addition, by using the contrast between the reflected light from the board and the shadowed free end of a pin, the inspection system may desirably be used to determine any axial twist of the pin as it extends outwardly from the board.

While the above uses of such inspection systems are required, it has been found that light is also randomly reflected from other surfaces such as other pins on the board, and onto surfaces of the pin being inspected and this randomly reflected light is received by the video camera. This affects the clarity of the image and may deleteriously affect the accuracy of the results of the inspection.

The present invention seeks to provide an illuminating device for an inspection system which reduces the above discussed problem.

Accordingly, the present invention provides an illumination device for an inspection system for inspecting circuit board pins extending from a printed circuit board comprising: a housing surrounding a passage for directing a camera along and from one end of the passage and axially onto a pin; a light source carried by the housing and surrounding the passage to direct an annular beam of light from one end of the housing around the pin and onto the board; and a shroud extending from the one end of the housing and axially of the passage beyond the light source while extending around the axis of the passage, the shroud provided to surround upper end regions of a pin under inspection and restrict light from being reflected onto said upper end regions.

The shroud may be formed of a tube such as a plastic or metal. The tube may be an extruded tube or may be formed from strip with its ends abutting or overlapped. If a tube is used, it should be telescopically movable within the housing so as to be pushed-up inside the housing if, for some reason, it is misaligned with a pin and engages the pin when the housing and pin are moved towards one another for the shroud to surround the pin. If the tube is telescopically movable, then preferably it is formed from a relatively heavy material, such as steel, to ensure that it will drop under its own weight out of telescoping relationship with the housing.

Alternatively, the shroud is provided by a brush with vertically extending bristles, the bristles lying close together to prevent passage of light between them and being arranged in annular formation with individual bristles resiliently deflectable upon contact with a pin.

The camera and a support for the printed circuit board are relatively movable to allow for the camera to traverse the board to inspect pins in succession. The camera and support are also relatively movable vertically to enable the shroud to be positioned around the upper end regions of each pin in turn. In one arrangement, the housing is also pivotal into and out of a vertical position and the shroud is telescopically movable within the housing so as to descend around a pin when the housing is moved into its vertical position. Movement of the housing out of the vertical position allows room for the pins in a board to be straightened before or after inspection.

One embodiment of the invention will now be described by way of example, with reference to the accompanying drawings, in which.

Figure 1:
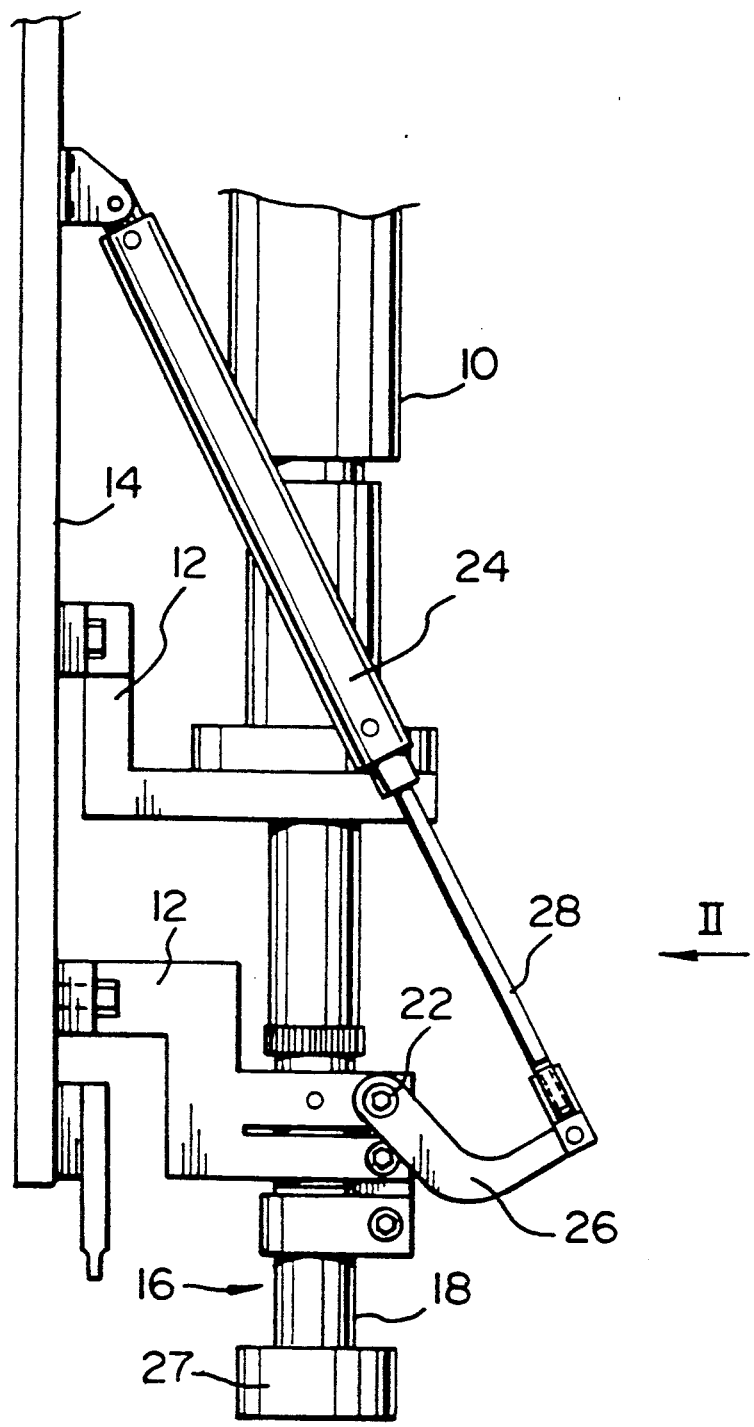
FIG. 1 is a side elevational view of part of an inspection system including an illuminating device according to the embodiment, the illuminating device being shown in a vertical position beneath a camera.
Figure 2:
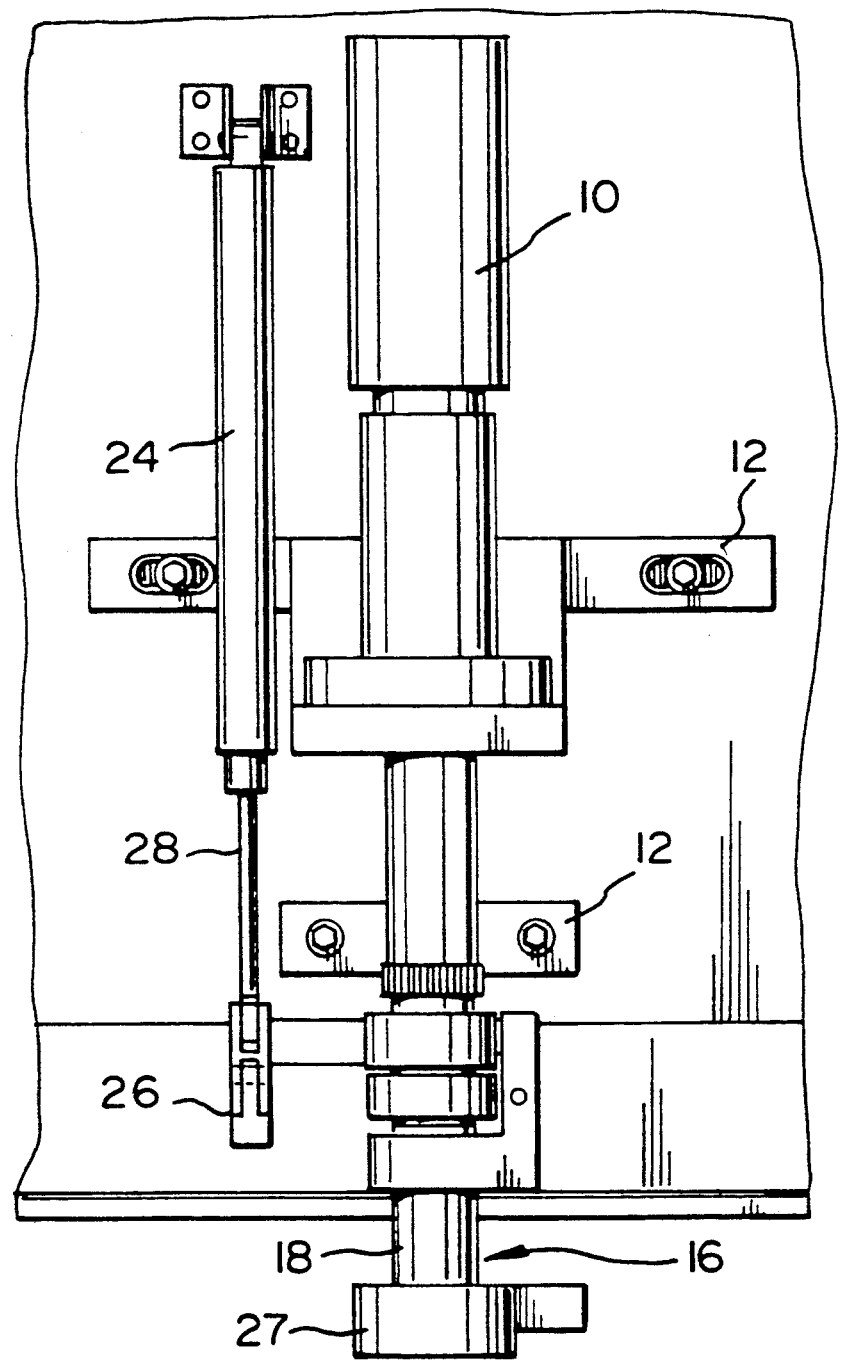
FIG. 2 is a front elevational view of the part of the inspection system and illuminating device in the direction of arrow II in FIG. 1.
Figure 3:
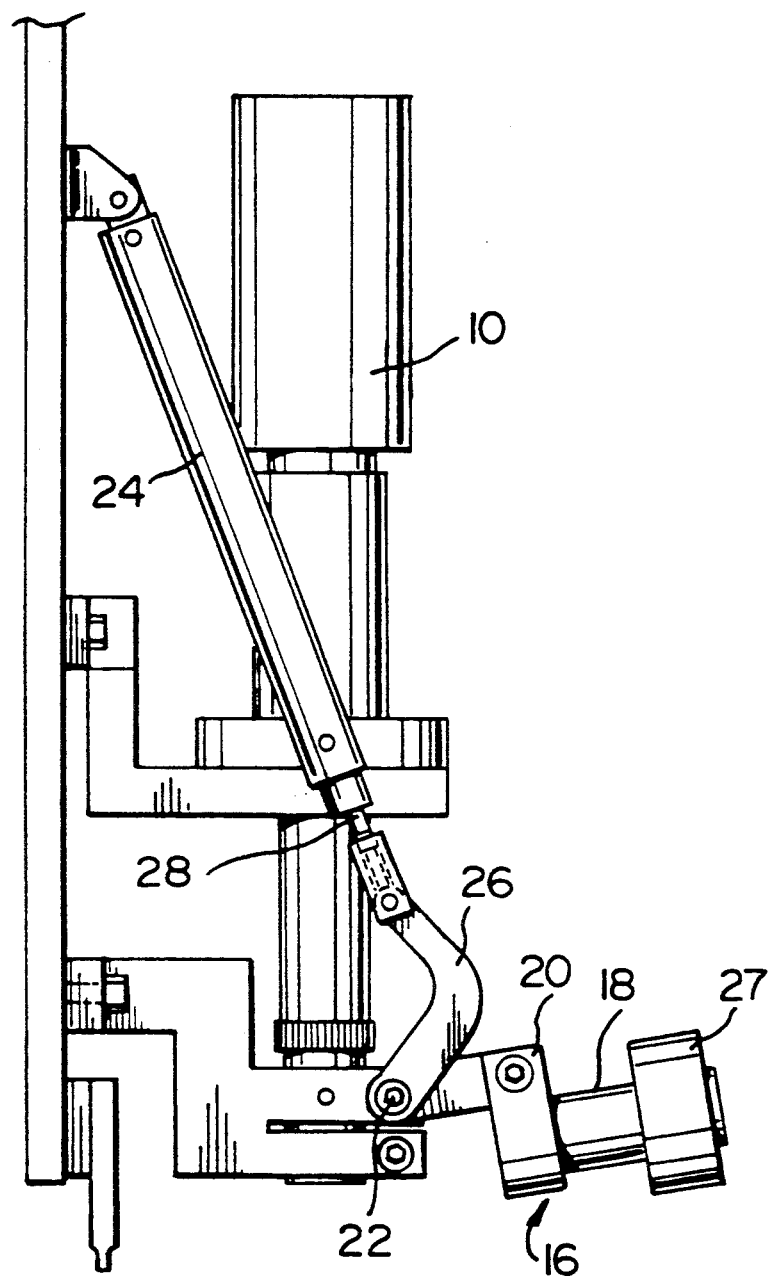
FIG. 3 is a view similar to FIG. 1 and showing the illuminating device in an alternative position; and, FIG. 4 is a cross-sectional view in side elevation of the illuminating device when in use and to a larger scale than that shown in FIG. 1.

In the embodiment as shown in FIGS. 1, 2 and 3 an inspection system for inspecting the positioning and twist of printed circuit board pins in a printed circuit board comprises a vertical camera structure 10 attached by vertically spaced support arms 12 to a vertical machine frame 14. The camera 10 is connected to a computer (not shown) which is programmed for analyzing data received by the camera and transmitted to the computer as electrical signals, the data relating to the twist and positioning of individual circuit board pins extending upwardly from a printed circuit board.

The inspection system also includes an illumination device 16 which is used to illuminate the upper surface of the printed circuit board, as will be described, so that the light reflected upwardly from the board is received by the camera and is contrasted by the upper end of the pin which lies in a shadowed region. The illuminating device 16 comprises a short cylinder 18 which is pivotally mounted by a mounting 20 about a horizontal axis 22. The illuminating device 16 is movable about the axis 22 by a moving means comprising a pneumatic or hydraulic cylinder 24 and a bell crank lever 26 extending from the piston rod 28 of the cylinder, the bell crank lever being itself attached to and pivotal together with the illuminating device at the axis 22. By means of the cylinder 24, the illuminating device is movable from a position in which the cylinder 18 forms a coaxial extension vertically beneath a downwardly facing camera lens (not shown) of the camera 10 as shown in FIG. 1 and a position in which it is orientated upwardly at an angle as shown in FIG. 3. The movement into the upward oriented position providing room over pins on the board for a pin straightening operation to be performed with a straightening bar.

The illumination device also comprises a housing 27 which is disposed at the lower end of and is carried by the cylinder 18 when the cylinder is in its vertical position shown in FIG. 1. As shown in more detail in FIG. 4, the housing 27 surrounds the end of the cylinder 18 thereby surrounding a passage 29 defined within the cylinder, the passage being 0.25 inches in diameter. The housing 27 carries a light source 30 which is of annular configuration formed by output ends of a multitude of optical fibers arranged in an annular formation shown for convenience as a solid annulus 30. The fibers collectively transmit light downwardly as an annular beam through an annular aperture 34 provided in the housing. This beam is divergent from the light source and through the aperture 34 as is indicated by the boundary lines 32 which represent the light.

In order to protect the upper end regions of any printed circuit board pin being inspected from reflected light in use of the inspection device, an annular shroud extends downwardly from the lower end of the housing 27 and thus below and beyond the light source 30. This shroud is in the form of a short steel tube 36 which has a large diameter upper end portion 37 telescopically received within the lower end of the cylinder 18. A lower end portion 39 has an inside diameter of 0.10 inches and is 0.010 inches thick so as to surround any particular pin under examination while being clear of other pins. The telescopic movement is provided so that the shroud will move upwardly upon contact with a pin in the event that it is moved downwards to surround the pin and there is shroud and pin misalignment. Thus damage to either the pin or the shroud is avoided.

In use of the inspection device, a printed circuit board 40 (FIG. 4) fitted with a plurality of circuit board pins 42 is supported on a horizontal support table 44 beneath the camera 10 and the illumination device 16. At this stage, the illumination device is inclined upwardly away from the table and the pins as shown by FIG. 3, to provide clearance beneath the camera to enable the pin straightening tool to be applied to the pins for straightening purposes in conventional manner. With the table and thus the printed circuit board 40 spaced a sufficient vertical distance below the camera 10, the illumination device 16 is then pivoted downwards to its operational position shown in FIG. 1 in which position the lower end of the tube 36 is above the upper ends of the pins 42.

Figure 4:
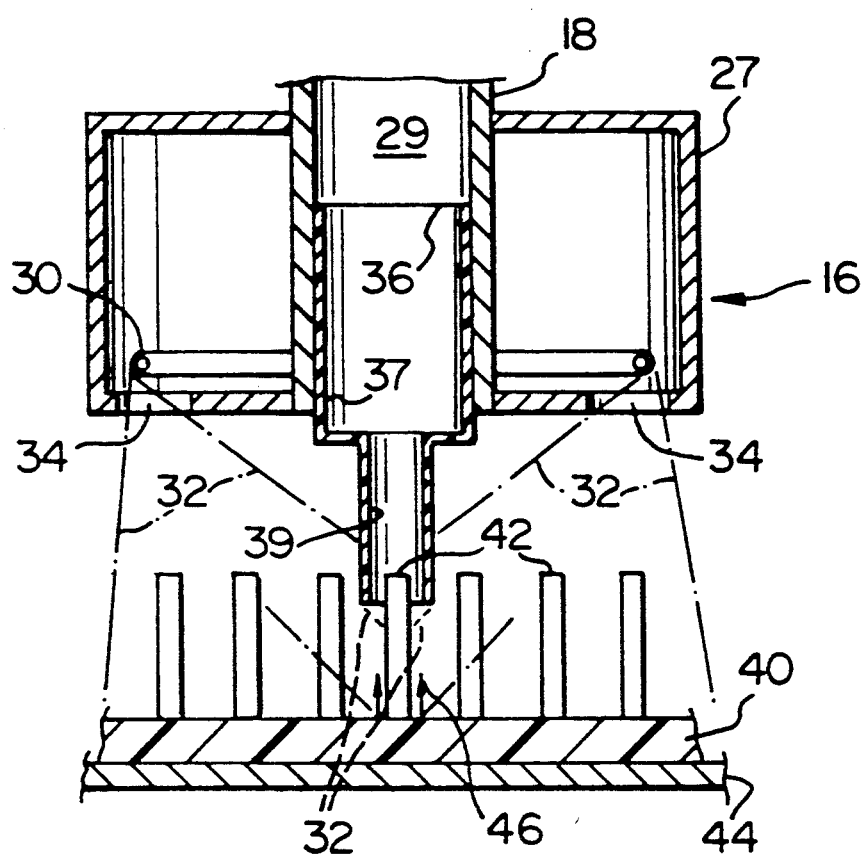

The machine is computer controlled and the computer is programmed to move the table horizontally intermittently in the 'y' direction to dispose the pins in a row in succession axially beneath the tube 36 and, after each horizontal movement of the table 42, the camera and illumination device 16 are lowered a sufficient distance to pass a pin within the lower end portion 39 of the tube 36 so that upper end regions of each pin are shrouded as shown by FIG. 4. After inspection of each individual pin, the camera and illumination device are then again raised to enable the horizontal table movement for the purpose of locating the next succeeding pin axially in alignment below the tube 36. For inspecting pins in other rows, the camera and illumination device are moved along the 'x' axis to align them with the other rows in turn.

As may be seen from FIG. 4, with a printed circuit board pin in its position for inspection by use of the camera 10, the light beam shines downwardly onto the board 40 and also shines onto and thus illuminates the lower end of the tube 36. This is shown by the boundary lines 32 of the light beam. The shroud thus prevents the light shining directly from the source 30 onto the upper end regions of the pin 42 so that this is maintained in shadow. In addition the tube 36 prevents any light from either the table or surrounding pins reflecting upwardly onto the upper end regions of the pin. As a result, during the inspection of any pin, the light received by the camera 10 is received solely by being reflected directly upwards from the board, as indicated by the arrows 46 in FIG. 4. The light thus shines directly alongside the pin under inspection through the tube 36 and to the camera lens. As the pin is itself in darkness at its upper end regions then a clear image of the shape of this upper end is received by the camera as it is in direct contrast to the reflected light received from the board. A clear boundary for the edge of the pin is delineated by the light passing around the pin and into the camera. The clarity of the image is assisted where the inside surface of the tube 36 is itself of a dark non-reflective nature such as a black matte or flat finish to the surface.

It follows therefore that positive signals may be sent by the camera to the computer for analysis, these signals being representative of a clear image of the upper end regions of the pin so that the horizontal position of the upper end regions and any twist in the pin may be accurately recorded.

What is claimed is:

1. An illumination device for an inspection system for inspecting circuit board pins extending from a printed circuit board comprising:

a housing surrounding a passage for directing a camera along and from one end of the passage and axially onto a pin;

a light source carried by the housing and surrounding the passage to direct an annular beam of light from one end of the housing around the pin and onto the board; and a shroud extending from the one end of the housing and axially of the passage beyond the light source while extending around the axis of the passage, the shroud provided to surround upper end regions of a pin under inspection and restrict light from being reflected onto said upper end regions.

2. An illumination device according to claim 1 wherein the shroud is resiliently flexible so as to be resiliently deflected upon moving into contact with a printed circuit board pin.

3. An illumination device according to claim 2 wherein the shroud is formed from a thin walled metal.

4. An illumination device according to claim 3 wherein the shroud is telescopically received within the housing so as to move into the housing of an end of a pin contacts 5. An illumination device according to claim 2 wherein the shroud is formed by bristles arranged in an annular formation and individual bristles are resiliently deflectable upon contact with a pin.

* * * * *